United States Patent [19]

Schwartz

[11] Patent Number: 4,980,352

[45] Date of Patent: Dec. 25, 1990

[54] GEM-DIMETHYL SUBSTITUTED BICYCLIC COMPOUNDS USEFUL AS EUKALEMIC DIURETICS

[75] Inventor: John A. Schwartz, Macclesfield, United Kingdom

[73] Assignee: ICI Americas Inc., Wilmington, Del.

[21] Appl. No.: 354,524

[22] Filed: May 19, 1989

[30] Foreign Application Priority Data

May 25, 1988 [GB] United Kingdom ................ 8812342

[51] Int. Cl.$^5$ ................ A61K 31/495; C07D 241/20; C07D 241/16
[52] U.S. Cl. .................................... 514/253; 514/255; 514/869; 544/405; 544/406; 544/407
[58] Field of Search ................ 544/405, 406, 407; 514/253, 255, 869

[56] References Cited

U.S. PATENT DOCUMENTS

| | | | |
|---|---|---|---|
| 3,305,552 | 2/1967 | Cragoe, Jr. et al. | 260/250 |
| 3,544,568 | 12/1970 | Cragoe, Jr. et al. | 260/247.2 |
| 3,577,418 | 5/1971 | Cragoe, Jr. et al. | 260/250 |
| 3,794,734 | 2/1974 | Cragoe, Jr. et al. | 424/330 |
| 3,809,721 | 5/1974 | Schultz et al. | 260/570.9 |
| 3,928,624 | 12/1975 | Cragoe, Jr. et al. | 424/330 |
| 4,029,816 | 6/1977 | Cragoe, Jr. et al. | 424/316 |
| 4,085,211 | 4/1978 | Cragoe, Jr. et al. | 424/250 |
| 4,272,537 | 6/1981 | Woltersdorf, Jr. et al. | 424/249 |
| 4,399,138 | 8/1983 | Barlow et al. | 424/250 |
| 4,550,111 | 10/1985 | Barlow et al. | 514/255 |

FOREIGN PATENT DOCUMENTS

| | | |
|---|---|---|
| 0057572 | 8/1982 | European Pat. Off. . |
| 0086564 | 8/1983 | European Pat. Off. . |
| 1181288 | 6/1967 | United Kingdom . |
| 2067195 | 1/1981 | United Kingdom . |

OTHER PUBLICATIONS

Smith, R. L. et al., *Diuretics—Chemistry, Pharmacology, and Medicine*, "2-Aminomethylphenols: A New Class of Saluretic Agents", pp. 93-124.

Stokker, G. E. et al., *J. Med. Chem.*, (1980) 23, 1414-1427.

*Primary Examiner*—Cecilia Shen
*Attorney, Agent, or Firm*—Thomas E. Jackson; James T. Jones

[57] ABSTRACT

Certain gem-dimethyl substituted bicyclic phenolic pyrazines of formula III possess eukalemic diuretic properties. They are of value in treating those diseases and conditions in which a eukalemic diuretic effect is required, for example in treating edema, hypertension and/or related conditions.

11 Claims, No Drawings

GEM-DIMETHYL SUBSTITUTED BICYCLIC COMPOUNDS USEFUL AS EUKALEMIC DIURETICS

This invention comprises novel gem-dimethyl substituted bicyclic compounds which are useful as eukalemic diuretics.

A variety of agents are available for use in treating hypertension. One particular class of such agents is diuretics. Diuretics are used for a variety of purposes, for example, reduction of fluid from the body and reduction of sodium levels in the body, for example, in the treatment of hypertension and edema.

A problem with some diuretics is the reduction of serum potassium levels and complications caused from reductions of potassium beyond levels needed for maintaining physiological functions. Thus, some diuretics are used in conjunction with a potassium conserving agent such as 3,5-diamino-N-(aminoiminomethyl)-6-chloropyrazine carboxamide monohydrochloride, dihydrate of formula II (formula set out, together with other formulae referred to by Roman numerals, on pages following Examples) described in U.S. Pat. No. 3,577,418 which is used in conjunction with, for example, thiazide diuretics.

There is thus a need for a single agent which is an effective but potassium-conserving (isokalemic, also called eukalemic) diuretic, such that it obviates the problems associated with hypokalemia (potassium depletion) and hyperkalemia (potassium buildup) without the need for taking multiple therapeutic agents.

A series of pyrazine-carboxamides has been described in U.S. Pat. No. 4,085,211 as eukalemic agents possessing diuretic and natriuretic properties. We have now discovered (and this is a basis for our invention) that, surprisingly, certain gem-dimethyl substituted bicyclic phenolic pyrazines of the formula III defined below possess eukalemic diuretic properties and are of value in treating those diseases and conditions in which a eukalemic diuretic effect is required, for example in treating edema, hypertension and/or related conditions.

SUMMARY OF THE INVENTION

According to the invention, there are provided compounds of formula III wherein:

One of $R^1$ and $R^2$ is a radical Z wherein Z is chloro, bromo, iodo, trifluoromethyl, methylsulfonyl or aminosulfonyl of formula $-SO_2NR^{10}R^{11}$ in which $R^{10}$ and $R^{11}$ are independently hydrogen or (1-5C)alkyl;

the other of $R^1$ and $R^2$ is a group of formula IV in which A is chloro or bromo, $R^4$ is hydrogen or (1-5C)alkyl, n is 1 or 2, p is 0 or 1, and R is hydrogen or methyl;

X is methylene, oxygen or sulfur; and m is 1, 2, or 3;

and the pharmaceutically acceptable salts thereof.

A particular value for $R^4$, $R^{10}$ or $R^{11}$ when it is (1-5C)alkyl is, for example, methyl, ethyl or propyl.

Preferred values for certain groups described above include, for example:

$R^4$: methyl;
for Z: bromo; and
for A: chloro.

Preferred compounds include:
(a) 3,5-diamino-N-[2-[[2-[[(6-bromo-2,3-dihydro-5-hydroxy-1,1-dimethyl-1H-inden-4-yl)methyl]amino]ethyl]methylamino]ethyl]-6-chloropyrazinecarboxamide; and (b) 3,5-diamino-N-[2-[[2-[[(9-bromo-2,3,4,5-tetrahydro-8-hydroxy-5,5-dimethyl-1-benzoxepin-7-yl)methyl]amino]ethyl]methylamino]ethyl]-6-chloropyrazinecarboxamide (Example 5);

and the pharmaceutically acceptable salts thereof

It will be appreciated that certain of the compounds of formula III, for example those containing an asymmetrically substituted carbon atom, may exist in, and be isolated in, optically-active and racemic forms. Some compounds may exhibit polymorphism. It is to be understood that the present invention encompasses any racemic, optically-active, tautomeric, polymorphic or stereoisomeric form, or mixtures thereof, which form possesses the properties described above, it being well known in the art how to prepare optically-active forms (for example, by resolution of the racemic form or by synthesis from optically-active starting materials) and how to establish the diuretic properties thereof (for example, using one of the test procedures described herein).

It is to be understood that the generic term "(1-5)alkyl" includes both straight and branched chain alkyl radicals but references to individual alkyl radicals such as "propyl" embrace only the straight chain ("normal") radical, branched chain isomers such as "isopropyl" being referred to specifically.

The compounds of the present invention may be prepared by methods which include those known in the chemical art. Such processes for the manufacture of a compound of formula III as defined above are provided as further features of the invention and include the following procedures in which the meanings of the generic radicals are defined above, other radicals have the meanings defined below, and "Pyz" has the meaning shown in formula V:

(A) Reductively alkylating a corresponding amine of formula XI with an appropriate carbonyl compound of formula XII wherein one of $R^5$ and $R^6$ is a radical Z and the other of $R^5$ and $R^6$ is a group of formula RCO—. The alkylation is preferably carried out, for example, in a solvent such as methanol or ethanol, by the in situ formation of a corresponding intermediate imine which is not isolated but directly reduced with a reducing agent such as sodium borohydride or hydrogen and a catalyst.

(B) Alkylating a corresponding amine of formula XI with an appropriate benzyl halide of formula XII wherein one of $R^5$ and $R^6$ is a radical Z and the other of $R^5$ and $R^6$ is a group of formula RCHCl—. The alkylation is preferably carried out in the presence of a base such as, for example, potassium carbonate or triethylamine, for example, for 1 to 5 days at, for example, room temperature in a solvent such as methanol or dimethylformamide.

(C) Reacting a corresponding amine of formula XI and an aldehyde of formula RCHO with an appropriate compound of formula XII wherein one of $R^5$ and $R^6$ is radical Z and the other of $R^5$ and $R^6$ is hydrogen. The reaction may be carried out, for example, under Mannich conditions, such as by heating at temperatures up to 100° C. for 1 to 5 days in an alcoholic or aqueous solution with an optional co-solvent such as tetrahydrofuran or dioxane.

(D) For a compound of formula III wherein Z is chloro, bromo or iodo, halogenating a corresponding compound of formula XII wherein one of $R^5$ and $R^6$ is hydrogen and the other of $R^5$ and $R^6$ is a group of formula IV. The halogenation may be carried out by using a conventional halogenating agent in an appropriate solvent such as, for example, acetic acid or methylene chloride.

(E) O-Dealkylating a corresponding aryl ether of formula XVIII wherein one of $R^5$ and $R^6$ is a radical Z and the other of $R^5$ and $R^6$ is a group of formula IV and $R^9$ is lower alkyl, such as, for example, methyl, with a conventional 0-dealkylating agent such as, for example, lithium thioethoxide in dimethylformamide or boron tribromide in methylene chloride.

(F) For a compound of formula III wherein p=1, acylating a corresponding amine of formula XII wherein one of $R^5$ and $R^6$ is a radical Z and the other of $R^5$ and $R^6$ is a group of formula $H_2N-(CH_2)_2-NH-CHR-$ with an ester of formula IX wherein L is a lower alkyl group, for example, methyl. The reaction may be carried out, for example, by mixing the reagents and heating at temperature up to 140° C. for 1 to 5 hours.

(G) For a compound of formula III wherein p=1 and R is methyl, treating a corresponding intermediate imine of formula XII wherein one of $R^5$ and $R^6$ is a radical Z and the other $R^5$ and $R^6$ is a group of formula XVII with an organometallic reagent such as, for example, methylmagnesium bromide, methylmagnesium chloride or methylmagnesium iodide.

(H) For a compound of formula III wherein p=0, acylating an amine of formula XII wherein one of $R^5$ and $R^6$ is a radical Z and the other $R^5$ and $R^6$ is a group of formula $H_2N-(CH_2)_2-N(R^4)-(CH_2)_2-NH-CHR-$ with a pyrazinoyl imidazole of formula VI.

The above-described starting materials may be made by conventional methods of organic chemistry, as well as by methods analogous to those described above, below or in the Examples.

Pyrazinoic acids of formula $PyzCO_2H$ may be prepared by the hydrolysis of the corresponding methyl esters of formula $PyzCO_2CH_3$. The hydrolysis is usually carried out using a solution of aqueous base such as sodium hydroxide and a solvent such as isopropanol or ethanol and stirring the mixture at room temperature for one to 24 hours. The pyrazinoic acid is then isolated by cooling and acidifying the mixture with an acid such as hydrochloric acid.

The pyrazinoyl imidazoles of formula VI are prepared by reacting the corresponding acids of formula $PyzCO_2H$ with 1,1-carbonyldiimidazole (slight excess) in a solvent such as dimethylformamide or methanol at room temperature and stirring the mixture for 10 to 24 hours. The pyrazinoyl imidazoles are isolated by dilution with methanol or water.

The pyrazinamides of formula VII are prepared by mixing the particular pyrazinoyl imidazole with an aliphatic diamine of formula VIII and stirring at ambient temperature from 5 to 24 hours. A solvent such as tetrahydrofuran may be added or an excess of the diamine may be used as the solvent. The desired reaction product is recovered by evaporating the solvent to provide the product which can be purified by crystallization from an alcohol such as ethanol.

Pyrazinamido esters of formula IX are prepared by mixing the particular pyrazinamide of formula VII with an appropriate alkyl bromoester of formula X (about 5-10% excess) where L is (1-3C)alkyl, for example, methyl, and a base such as potassium carbonate or triethylamine for 1 to 2 days at room temperature. (When n=2 in formula X, an acrylic ester of formula Xa may be substituted for the bromoester.) A solvent such as methanol or dimethylformamide is used. The pyrazinamido ester is isolated by diluting it with water. It can be purified by recrystallization from an appropriate solvent such as ethanol.

Pyrazinamidoamines of formula XI wherein p=1 are prepared by mixing the particular pyrazinamido ester of formula IX with ethylenediamine (twofold excess) and heating at temperatures up to 100° C., preferably about 40° C., for 1 to 24 hours. A solvent such as an alcohol, for example, 2-propanol may be added or an excess of the amine may be used as the solvent. The desired reaction product is recovered by evaporation of the solvent and excess diamine.

Another method for the preparation of a pyrazinamidoamine of formula XI wherein p=1 begins with an aliphatic diamine with one of the amino groups suitably protected (for example, either as a phthalimide or t-butyloxycarbonyl (BOC)). Such a compound is shown in formula XIII where Q is a suitable protecting group such as BOC or phthalimide. Acylation of this monoprotected diamine with a haloalkanoyl halide of formula XIV where Hal is chloro, bromo or iodo, in a solvent such as tetrahydrofuran or dioxane at ambient temperature in the presence of an acid scavenger such as triethylamine or potassium carbonate or 4-methylmorpholine, provides the acylated diamine of formula XV which may be purified by distillation. Alkylation of a suitable pyrazinamide of formula VII with the acylated diamine of formula XV and a base such as triethylamine or potassium carbonate either neat or in a solvent such as tetrahydrofuran or dimethylformamide provides the appropriate protected pyrazinamidoamine of formula XVI wherein p=1, which is isolated by diluting with water. It can be purified by crystallization from an appropriate solvent, Removal of the protecting group Q provides the corresponding pyrazinamidoamine of formula XI wherein p=1.

Pyrazinamidoamines of formula XI wherein p=0 are prepared by mixing an aliphatic haloamine of formula XIX where Hal is iodo, bromo or chloro and Q is a suitable protecting group, for example, phthalimide or t-butyloxycarbonyl (BOC), for example, such as shown in Formula XIXa, with the particular pyrazinamide of formula VII and a base such as potassium carbonate or triethylamine for 1 to 5 days at room temperature. A solvent such as methanol or dimethylformamide is used. The protected pyrazinamidoamine of formula XVI, wherein p=0, is isolated by diluting with water It can be purified by recrystallization from an appropriate solvent such as ethanol. Removal of the protecting group Q provides the corresponding pyrazinamidoamine of formula XI, wherein p=0.

Alternatively, pyrazinamidoamines of formula XI wherein p=0 also may be prepared by mixing the particular pyrazinoyl imidazolide of formula VI with an excess of an aliphatic triamine of formula XX in a solvent such as tetrahydrofuran. The desired reaction product is recovered by evaporating the solvent to provide the product. (For the preparation of selected aliphatic triamines, see U.S. Pat. No. 3,201,472).

The intermediate phenolic compounds of formula XII and the related ethers of formula XVIII may be prepared by conventional methods of aromatic and heteroaromatic chemistry. In U.K. Patent Application No. GB 2,067,195 A, for example, there is described the conversion of an ester of formula XXI wherein $R^9$ is methyl, $R^{10}$ is —COOCH$_3$, X is methylene and m is 1 to the corresponding carbinol of formula XXI wherein $R^9$ is methyl, $R^{10}$ is —C(CH$_3$)$_2$OH, X is methylene and m is 1, followed by acid catalyzed cyclization, using 85% phosphoric acid at 100° C., to afford the corresponding indane of formula XVIII wherein $R^5$ and $R^6$ are hydrogen, $R^9$ is methyl, X is methylene and m is 1. The methyl ether was cleaved using refluxing 63% hydrobromic acid to afford the corresponding phenol of formula XII wherein $R^5$ and $R^6$ are hydrogen, X is methylene and m is 1, which phenol was further converted inter alia into the corresponding phenols of formula XII wherein $R^5$ is acetyl and bromo.

In the Examples is described the preparation of ethers of formula XVIII wherein $R^5$ and $R^6$ are hydrogen, $R^9$ is methyl, X is oxygen and m is 1, 2, and 3 from the corresponding ethers of formula XXI wherein $R^{10}$ is —C(CH$_3$)$_2$OH (prepared from the corresponding ester wherein $R^{10}$ is —COOCH$_3$) by acid catalyzed cyclization using the preferred reagent phosphorous pentoxide in methanesulfonic acid at ambient temperature. (The use of hot 85% phosphoric acid resulted in destruction rather than cyclization).

Conversion of an ether of formula XVIII wherein $R^5$ and $R^6$ are hydrogen into a required ether of formula XVIII or phenol of formula XII wherein one of $R^5$ and $R^6$ is a radical Z (if required) and the other of $R^5$ and $R^6$ is a group of formula RCO (if required) may be carried out by an appropriate sequence of formylation (for R=hydrogen) or acetylation (for R=methyl) (if required), introduction of the radical Z (if required), and cleavage of the ether (if required), for example as described in the Examples.

An ether of formula XVIII wherein one of $R^5$ and $R^6$ is a radical Z and the other of $R^5$ and $R^6$ is a group of formula IV and $R^9$ is lower alkyl may be prepared from a corresponding ether of formula XVIII wherein one of $R^5$ and $R^6$ is a radical Z and the other of $R^5$ and $R^6$ is a group of formula RCO— and an appropriate amine of formula XI by reductive alkylation using a process similar to process (A), above.

A group of formula RCO— contained in an ether of formula XVIII or phenol of formula XII may be converted into a group of formula RCHCl— by a conventional method.

A phenol of formula XII wherein one of $R^5$ and $R^6$ is a radical Z and the other of $R^5$ and $R^6$ is a group of formula H$_2$N—(CH$_2$)$_2$—NH—CHR— may be prepared from a corresponding phenol of formula XII wherein one of $R^5$ and $R^6$ is a radical Z and the other of $R^5$ and $R^6$ is a group of formula RCO- by reductive alkylation of an amine of formula XIII using a procedure similar to process (A) above, followed by removal of the protecting group Q.

An intermediate imine of formula XII wherein one of $R^5$ and $R^6$ is a radical Z and the other of $R^5$ and $R^6$ is a group of formula XVII may be prepared by formation of the imine from an appropriate amine of formula XI and a corresponding phenol of formula XII wherein one of $R^5$ and $R^6$ is a radical Z and the other of $R^5$ and $R^6$ is a group of formula HCO— by a conventional method.

The benzylic triamines of formula XII wherein one of $R^5$ and $R^6$ is a radical Z and the other of $R^5$ and $R^6$ is a group of formula H$_2$N—(CH$_2$)$_2$—N(R$^4$)—(CH$_2$)$_2$—NH—CHR— are prepared by reductive alkylation of the particular aliphatic triamine of formula XX with an appropriate carbonyl compound of formula XII wherein one of $R^5$ and $R^6$ is a radical Z and the other of $R^5$ and $R^6$ is a group of formula RCO— using a procedure similar to that described in Method (A), above. The product may be purified by crystallization from a hydrocarbon solvent.

Pharmaceutically acceptable salts may be obtained using standard procedures well known in the art, for example, by reacting a compound of formula III with a suitable acid affording a physiologically acceptable anion, such as, for example, sulfuric, hydrochloric or citric acid.

As stated previously, the compounds of this invention or a salt thereof may be useful in the treatment of hypertension and particularly as diuretics, especially eukalemic diuretics. The compounds of formula III are of value as pharmacological standards for the development and standardization of new disease models and assays for use in developing new therapeutic agents for treating hypertension.

When used in the treatment of one or more of the above mentioned diseases, a compound of formula III or a salt thereof may generally be administered as an appropriate pharmaceutical composition which comprises a compound of formula III as defined hereinbefore or a salt thereof together with a pharmaceutically acceptable diluent or carrier, the composition being adapted for the particular route of administration chosen. Such compositions are provided as a further feature of the invention. They may be obtained by employing conventional procedures and excipients and binders and may be in a variety of dosage forms. For example, they may be in the form of tablets, capsules, solutions or suspensions for oral administration; in the form of suppositories for rectal administration; in the form of sterile solutions or suspensions for administration by intravenous or intramuscular injection or infusion; and in the form of powders together with pharmaceutically acceptable inert solid diluents such as lactose.

For oral administration a tablet or capsule containing up to 250 mg (and typically 5 to 100 mg) of a compound of formula III or a salt thereof may conveniently be used. Similarly, for intravenous or intramuscular injection or infusion a sterile solution or suspension containing up to 10% w/w (and typically 0.05 to 5% w/w) of a compound of formula III or a salt thereof may conveniently be used.

The dose of compound of formula III or a salt thereof to be administered will necessarily be varied according to principles well known in the art taking account of the route of administration and the severity of the condition and the size and age of the patient under treatment. However, in general, a compound of formula III or a salt thereof will be administered to a warm-blooded animal (such as man) so that a dose in the range of, for example, 0.05 to 25 mg/kg (and usually 0.5 to 10 mg/kg) is received.

The diuretic and eukalemic properties of a compound of formula III may be demonstrated by using standard tests.

Test A:

Method. Female Beagle dogs are selected from an established breeding colony (weight range 9.0–13.0 kg), placed on a special diet of certified dog food and one can of Prescription Diet P/D Dog Food, and observed for suitability for training. Dogs are selected from this group for training. Over a one to two week period the dogs are allowed to gradually build up tolerance to light restraint, standing, or sitting in a mesh sling support stand. Maximum time in sling is approximately 9 hours.

Also, relaxed acceptance of the process of urinary bladder catheterization is accomplished during the training period. Sterile Bardex foley catheters (sizes 8, 10 pediatric) are used. The conscious female Beagle dogs with free access to water are fasted overnight. The dogs are placed in sling support stands (Alice King Chatham) and catheterized. A short equilibration period of about 30 minutes allows time for residual urine to be drained from the bladder. Urine spontaneously voided is collected in 50 ml pre-weighed tubes (Falcon). Two 1-hour control periods are followed by oral dosing with gelatin capsules containing test compounds or standard diuretics. Alternatively, some compounds are administered via oral gauge tubes in 10 ml quantities. No water loading is done. Spontaneously voided urine is collected for an additional six hours for a total collection period of eight hours. Afterward, dogs are returned to cages and fed and watered. Experiments are conducted once every two weeks on each dog, thus assuring adequate recovery between tests Urine samples are weighed and measured for volume Analysis of urinary electrolytes (sodium, potassium, chloride) is done on the following day. The analysis of urinary electrolytes showed results similar to other diuretics except that there was no excessive potassium loss.

Test B:

Method: Beagle dogs obtained from the established breeding colony of Marshall Animal Facility or White Eagle Laboratories are utilized. Healthy male and/or female Beagles 9-13 kg in body weight are housed according to standard operating procedure (SOP) for Veterinary Services and are placed on a diet of "certified" dry dog food supplemented with one can of puppy diet (P/D) prescription Diet dog food, with free access to water. A two-week minimum period of equilibration on this diet is necessary before determination of basal level electrolytes is attempted.

Prior to beginning actual drug dosing, six control blood samples are obtained to establish a range for basal level electrolytes. Control samples are evaluated for consistency in plasma $K^+$ levels, and a range of less than 0.25 mEq of $K^+$ is usually desirable. Historically, plasma $K^+$ levels in the range of 4.00-4.30 mEq have been obtained. Any dog not approximating these values is normally dropped from the study.

Sampling Procedure: Plasma samples are obtained by forearm venopuncture via the saphenous vein or the jugular vein A 5 cc syringe with 20 gauge needle is used to obtain one 5 cc sample The sample is preserved with 100 μl of 1000 unit heparin. Samples are centrifuged for ten minutes at 2500 rpm. Plasma is then pipetted into an appropriately labeled tube and all samples are frozen to await electrolytes determination.

Drug Dosing Schedule and Preparation: After control samples are analyzed, the dogs are divided randomly into groups, allowing a minimum of four dogs per drug group. Test compounds are dosed on a mg/kg basis. Gelatin capsules size "2"00 and "3"000 are used. Alternatively, some compounds are administered via oral gauge tubes. Compounds are suspended in 10 ml of saline by sonicating. The weight of the dog is determined by averaging the values over the three days of controls. Time of day for drug dosing is consistent throughout the study. Samples are required on days 4, 7, 11, 14, and 21, and 28. Dosing takes place mid-morning (10 a.m. to 11 a.m.), and blood is drawn approximately three hours after dosing (1 p.m. to 2 p.m ). (Drug capsules are dosed orally followed by 5-10 milliliters of water from a syringe with oral dosing needle attached ) Hematocrits are taken with Microhematocrit capillary tubes and read immediately following collection of plasma samples.

Data Evaluation: Plasma samples are analyzed for potassium, as described above and showed no substantial change in serum potassium.

In general, the compounds of this invention which were tested showed a profile as eukalemic diuretics. Compounds of this invention which were tested have not shown any signs of overt toxicity following oral administration at a dose several multiples of the recommended therapeutic dose.

The invention will now be illustrated by the following non-limiting examples in which, unless stated otherwise:

(i) all operations were carried out at room or ambient temperature, that is, at a temperature in the range of 18°-25° C.:

(ii) evaporation of solvent was carried out using a rotary evaporator under reduced pressure (600-4000 pascals 4.5-30 mm Hg) with a bath temperature of up to 60° C.;

(iii) flash chromatography was carried out on Merck Kieselgel (Art 9385) and column chromatography on Merck Kieselgel 60 (Art 7734); [these materials were obtained from E. Merck, Darmstadt, W. Germany]; thin layer chromatography (TLC) was carried out on Analtech 0.25 mm silica gel GHLF plates (Art 21521), obtainable from Analtech, Newark, Del., U.S.A.;

(iv) in general, the course of reactions was followed by thin layer chromatography (TLC) an reaction times are given for illustration only;

(v) melting points are uncorrected and (d) indicates decomposition; the melting points given are those obtained for the materials prepared as described; polymorphism may result in isolation of materials with different melting points in some preparations;

(vi) all final products were essentially pure by TLC and microanalytical date;

(vii) yields are given for illustration only;

(viii) reduced pressures are given as absolute pressures in pascals (Pa); other pressures are given as gauge pressures in bars;

(ix) chemical symbols have their usual meanings; the following abbreviations have also been used: v (volume), w (weight), mp (melting point), 1 [liter(s)], ml (milliliters), g [gram(s)], mg milligram(s)];

(x) solvent ratios are given in volume: volume (v/v) terms;

(xi) TLC solvent systems Solvent System A: 25:5:70 (v/v/v) methanol:triethylamine:methylene chloride;

(xii) some compounds are denoted by letters for example, (A), for later reference in the Examples; and (xiii) drying the organic phase was accomplished by swirling with sodium sulfate.

EXAMPLE 1

3,5-Diamino-N-[2-[[2-[[(6-bromo-2,3-dihydro-5-hydroxy1,1-dimethyl-1H-inden-4-yl)methyl]amino]ethyl]methylamino]ethyl]-6-chloropyrazinecarboxamide.

(a) A mixture of 1.82 g (6.32 mmol) of 3,5-diamino-N-[2-[(2-aminoethyl)methylamino]ethyl]-6 -chloropyrazinecarboxamide (A) and 1.70 g (6.32 mmol) of 6-bromo-1,1-dimethyl-5-hydroxyindan-4-carboxaldehyde (B) in 70 ml of ethanol and 10 ml of methylene chloride was stirred at ambient temperature for 1 h. Sodium borohydride (0.29 g, 7.58 mmol) was added and the reaction mixture stirred for 15 min. The solution was evaporated and the residue was partitioned between water and methylene chloride The organic phase was dried and evaporated. The residue was chromatographed on silica gel (150 g) using 0.2:3:96.8 (v/v/v) ammonium hydroxide:methanol:methylene chloride as eluent. There was obtained 2.62 g (4.84 mmol, 77%) of the title compound after trituration with ether: mp 134°–136° C.

Analysis calculated for: $C_{22}H_{31}BrClN_7O_2$: C, 48.85: H, 5.78: N, 18.13. Found: C, 48.87: H, 5.79: N, 18.15.

(b) The material from Example 1(a) was converted into a hydrochloride salt in methanol; mp 173°–175° C.

Analysis calculated for: $C_{22}H_{31}BrClN_7O_2.2HCl.1-H_2O$: C, 41,82; H, 5.58; N, 15.52. Found: C, 41.99; H, 5.40; N, 15.62.

(c) The starting material (A) was obtained as follows:

To a stirred solution of 84.0 g (0.744 mol) of N-(2-aminoethyl)-N-methyl-1,2-ethanediamine (see U.S. Pat. No. 3,201,472 for a method of obtaining this compound) in 700 ml of tetrahydrofuran was added 88.6 g (0.372 mmol) of 1-(3,5-diamino-6-chloropyrazinoyl)imidazole in 10 portions over 1 5 h. After 1 h at ambient temperature the reaction mixture was filtered and concentrated to 300 ml. The solution was added dropwise to 1.4 liters of ether with vigorous stirring. The solid was filtered, washed with ether and dried. There was obtained 74.3 g (0.258 mol, 70%) of 3,5-diamino-N-[2-[(2-aminoethyl)-methylamino]ethyl]-6-chloropyrazinecarboxamide. A sample was filtered through a pad of silica gel and eluted with 5:95 (v/v) methanol:methylene chloride saturated with ammonia gas mp 138°–139.5° C.

Analysis calculated for: $C_{10}H_{18}ClN_7O$: C, 41.74; H, 6.31; N, 34.07. Found: C, 41.53; H, 6.15; N, 33.72.

(d) The starting material (B) was obtained as follows:

A mixture of 7.87 g (32.6 mmol) of 6-bromo-1,1-dimethylindan-5-ol (see U.K. Patent Application No. GB 2,067,195 A for a method of obtaining this compound) and 7.16 g (51.0 mmol) of hexamethylenetetramine was refluxed in 100 ml of trifluoroacetic acid for 5 h. The solution was cooled to ambient temperature and diluted with 300 ml of water. The aqueous residue was extracted with methylene chloride. The organic phase was washed with saturated sodium bicarbonate solution dried and evaporated. The residue was chromatographed on silica gel (100 g) using a gradient from hexane to 1:99 (v/v) ether:hexane as eluent. There was obtained 1.7 g (6.32 mmol, 19%) of 6-bromo-1,1-dimethyl-5-hydroxyindan-4-carboxaldehyde as a light yellow solid mp 42°–143° C.

Analysis calculated for $C_{12}H_{13}BrO_2$: C, 53.55; H, 4.87. Found: C. 53.58 H, 4.87.

EXAMPLES 2–5

The procedure described in Example 1 was repeated using corresponding benzaldehydes of formula XII wherein $R^5$=CHO, $R^6$=Br, and X and m have the values shown in Table I to give products of formula III wherein $R^1$=IV, A=Cl, $R^4$=CH , p=0, R=H, $R^2$=Br and X and m have the values shown in Table I:

TABLE I

| Example | X | m | mp °C. Free Base | % Yield | salt | mp °C. salt |
|---|---|---|---|---|---|---|
| 2 | CH$_2$ | 1 | 141–142 | 68 | di-HCl | 164–165 |
| 3 | O | 1 | 131–132 | 27 | oxalate | 160–161 |
| 4 | O | 2 | 143.5–144.5 | 86 | di-HCl | 205–207 |
| 5 | O | 3 | 139.5–140.5 | 79 | di-HCl | 171–173 |

EXAMPLE 6

The benzaldehyde used in Example 2 was prepared as follows:

(a) To a mixture of 10.60 g (60.0 mmol) of 5-methoxy-1,1-dimethylindane (see U.K. Patent Application No. GB 2,067,195 A for a method of obtaining this compound) and 6.5 g (90.0 mmol) of dimethylformamide was added 11.5 g (75.0 mmol) of phosphorous oxytrichloride. The mixture was heated at 100° C. for 5 h. The reaction mixture was cooled to ambient temperature and poured onto 100 g of ice. The aqueous residue was extracted with ether. The organic phase was washed with saturated sodium bicarbonate solution, dried and evaporated. The residue was chromatographed on silica gel (70 g) using a gradient from hexane to 2:98 (v/v) ether:hexane as eluent, There was obtained 4.86 g (23.8 mmol, 40%) of 1,1-dimethyl-5-methoxyindan-6-carboxaldehyde as a white solid after crystallization from hexane mp 51°–52° C.

Analysis calculated for: $C_{13}H_{16}O_2$: C, 76.44; H, 7.89. Found: C, 76.23: H, 7.81.

(b) To a solution of 4.25 g (20.8 mmol) of 1,1-dimethyl-5-methoxyindan-6-carboxaldehyde in 25 ml of methylene chloride and cooled in an ice water bath was added 22 ml (22.0 mmol, 1M in methylene chloride) of boron tribromide. After stirring for 1 h, the reaction mixture was poured into 100 ml of ice water The organic phase was dried and evaporated. The residue was chromatographed on silica gel (50 g) using hexane as eluent There was obtained 3.37 g (17.7 mmol, 85%) of 1,1-dimethyl-5-hydroxyindan-6-carboxaldehyde as a white solid; mp 40°–40.5° C.

Analysis calculated for: $C_{12}H_{14}O_2$: C, 75.76: H, 7.42. Found: C, 75.62: H, 7.42.

(c) A solution of 3.1 g (16.3 mmol) 1,1-dimethyl-5-hydroxyindan-6-carboxaldehyde and 3.1 g (17.4 mmol) of N-bromosuccinimide in 50 ml of methylene chloride was stirred at ambient temperature for 2 days. Water (50 ml) was added. The organic phase was dried and evaporated. The residue was filtered through silica gel (20 g) using a gradient from hexane to 2:98 (v/v) ether:hexane as eluent. There was obtained 4.0 g (14.8 mmol, 91%) of 4-bromo-1,1-dimethyl-5-hydroxyindan-6-carboxaldehyde as yellow crystals after crystallization from ethanol; mp 77.5°–78.5° C.

Analysis calculated for $C_{12}H_{13}BrO_2$: C, 53.55: H, 4.87. Found C, 53.31 H, 4.86.

EXAMPLE 7

The benzaldehyde used in Example 3 was prepared as follows:

(a) To a solution of 51.0 g (0.26 mol) of methyl 2-(3-methoxyphenoxy)acetate in 750 ml of ether and cooled in an ice water bath was added dropwise a solution of 22 ml (0.65 mmol, 2.9 M) of methylmagnesium bromide in ether. After 0.5 h the reaction mixture was poured into 500 ml of 2N hydrochloric acid. The organic phase was dried and evaporated. The residue was vacuum distilled providing 49.0 g (0.25 mol, 96%) of 1-(3-methoxyphenoxy)-2-methyl-2-propanol as a colorless oil: bp 115°–135° C. at 33 Pa.

(b) A sample of this alcohol was converted into a p-nitrobenzoate ester mp 84°–86° C.

Analysis calculated for $C_{18}H_{19}NO_6$: C, 62.60: H, 5.55: N, 4.06. Found: C, 62.82: H, 5.61: N, 4.04.

(c) To a solution of 50 g (0.352 mol) of phosphorous pentoxide in 500 ml of methanesulfonic acid was added dropwise 20 g (0.101 mol) of 1-(3-methoxyphenoxy)-2-methyl-2-propanol over a 30 min period. The reaction mixture was stirred for 3 h at ambient temperature. The reaction mixture was poured into 1.5 l of ice water and extracted with ether. The combined extracts were dried and evaporated. The residue was filtered through silica gel (500 g) using a gradient from hexane to 10:90 (v/v) of ether:hexane as eluent, There was obtained 13.2 g (74.06 mmol, 72%) of 2,3-dihydro-6-methoxy-3,3-dimethylbenzofuran. This material was dissolved in 75 ml of toluene an 8.12 g (0.11 mol) of dimethylformamide was added. The mixture was cooled in an ice water bath and 14.23 g (92.8 mmol) of phosphorous oxytrichloride was added dropwise. The reaction mixture was heated at reflux for 3 h. The reaction mixture was cooled to ambient temperature and poured into 300 ml of 2N sodium hydroxide solution. The organic phase was washed with 1N hydrochloric acid, water, saturated sodium chloride solution, dried and evaporated. The residue was chromatographed on silica gel (150 g) using a gradient of from hexane to 25:75 (v/v) ether:hexane as eluent. There was obtained 10.3 g (49.9 mmol, 68%) of 2,3-dihydro-6-methoxy-3,3-dimethyl-5-benzofurancarboxaldehyde as white crystals; mp 75°–76° C.

Analysis calculated for: $C_{12}H_{14}O_3$: C, 69.89; H, 6.84. Found: C, 69.92: H, 6.74.

(d) To a solution of 10.4 g (50.4 mmol) of 2,3-dihydro-6-methoxy-3,3-dimethyl-5-benzofurancarboxaldehyde in 250 ml of methylene chloride and cooled to −78° C. was added dropwise 51.0 ml (51.0 mmol, 1M in methylene chloride) of boron tribromide. The reaction mixture was warmed to ambient temperature and stirred for 1 day. The reaction mixture was poured into 500 ml of water. The organic phase was washed with saturated sodium bicarbonate solution, dried and evaporated. The residue was chromatographed on silica gel (250 g) using a gradient from 2:1 (v/v) hexane:methylene chloride to methylene chloride as eluent. There was obtained 5.77 g (30.0 mmol, 59%) of 2,3-dihydro-6-hydroxy-3,3-dimethyl-5-benzofurancarboxaldehyde as a white solid mp 100°–102° C.

Analysis calculated for: $C_{11}H_{12}O_3$: C, 68.74: H, 6.29. Found: C, 68.75: H, 6.29.

(e) A solution of 5.27 g (27.4 mmol) of 2,3-dihydro-6-hydroxy-3,3-dimethyl-5-benzofurancarboxaldehyde and 5.86 g (32.9 mmol) of N-bromosuccinimide in 135 ml of methylene chloride was stirred at ambient temperature for 3 h. Water (400 ml) was added. The organic phase was dried and evaporated. The residue was chromatographed on silica gel (150 g) using a gradient from 20:80 (v/v) ether:hexane to 40:60 (v/v) ether:hexane eluent. There was obtained 7.0 g (25.8 mmol, 94%) of 7-bromo-2,3-dihydro-6-hydroxy-3,3-dimethyl-5-benzofurancarboxaldehyde. A sample was crystallized from toluene: mp 152°–154° C.

Analysis calculated for $C_{11}H_{11}BrO_3$: C, 48.73: H, 4.09. Found C, 48.87; H, 4.12.

EXAMPLE 8–9

The benzaldehydes used in Examples 4 and 5 were prepared as follows:

(a) The procedure used in Example 7(a) was repeated using methyl 3-(3-methoxyphenoxy)propionate and methyl 4-(3-methoxyphenoxy)butyrate, respectively, to give 1-(3-methoxyphenoxy)-3-methyl-3-butanol (Example 8(a)) and 1-(3-methoxyphenoxy-4-methyl-4-pentanol (Example 9(a)), respectively, as shown in Table II.

The alcohols were further characterized as their respective p-nitrobenzonate esters as shown in Table II.

TABLE II

| Example | % Yield | mp °C. p-nitrobenzoate ester | Analysis p-nitrobenzoate ester |
|---------|---------|------------------------------|-------------------------------|
| 8(a)    | 96.2    | 104.5–105.5                  | $C_{19}H_{21}NO_6$:C, 63.50; H, 5.89; N, 3.90 Found:C, 63.42; H, 5.98; N, 3.77 |
| 9(a)    | 100     | 70–71                        | $C_{20}H_{23}NO_6$:C, 64.33; H, 6.21; N, 3.75 Found:C, 64.37; H, 6.19; N, 3.71 |

(c) The procedure used in Example 7(c) was repeated using the respective 3-methoxyphenoxyalkanols of Examples 8(a) and 9(a) to give the corresponding products of formula XVIII wherein $R^5$=CHO, $R^6$=H, $R^9$=$CH_3$, X=O and m has the values shown in Table III.

TABLE III

| Example | m | % Yield | mp °C. | Analysis |
|---------|---|---------|--------|----------|
| 8(c)    | 2 | 74      | 77.5–79| $H_{13}H_{16}O_3$:C, 70.89; H, 7.32 Found: C, 70.91; H, 7.27 |
| 9(c)    | 3 | 74.5    | 85–86  | $C_{14}H_{18}O_3$:C, 71.79; H, 7.74 Found:C, 71.75; H, 7.77 |

(d) The procedure of Example 7(d) was repeated using the products of Examples 8(c) and 9(c) to give the corresponding products of formula XXI wherein $R^5$=CHO, $R^6$=H, X=O and m has the values shown in Table IV.

TABLE IV

| Example | m | % Yield | mp °C.  | Analysis |
|---------|---|---------|---------|----------|
| 8(d)    | 2 | 87      | 121–122 | $C_{12}H_{14}O_3$:C, 69.89; H, 6.84 Found:C, 69.95; H, 6.86 |
| 9(d)    | 3 | 70      | 113–115 | $C_{13}H_{16}O_3$:C, 70.89; H, 7.32 Found:C, 70.93; H, 7.30 |

(e) The procedure used in Example 7(e) was repeated using the products of Examples 8(d) and 9(d) to give the corresponding products of formula XII wherein $R^5$=CHO, $R^6$=Br, X=O and m has the values shown in Table V.

TABLE V

| Example | m | % Yield | mp °C.    | Analysis |
|---------|---|---------|-----------|----------|
| 8(e)    | 2 | 82      | 154–155   | $C_{12}H_{13}BrO_3$:C, 50.55; H, 4.60 Found:C, 50.56; H, 4.61 |
| 9(e)    | 3 | 60      | 118.5–120 | $C_{13}H_{15}BrO_3$:C, 52.19; H, 5.05 Found:C, 52.20; H, 5.03 |

EXAMPLE 10

Each capsule contains:

| Material | Quantity/350 mg Blend |
|---|---|
| Compound of Formula III | 120.0 mg. |
| Lactose, National Formulary (NF) Fast Flo | 175.0 mg. |
| Sodium starch glycolate, NF | 18.0 mg. |
| Pregelatinized starch, NF | 35.0 mg. |
| Magnesium stearate, NF | 2.0 mg. |

All of the above-listed materials, except the magnesium stearate, are screened through a suitable screen, for example, 20 mesh, and blended in a mixer for about 5 minutes. The magnesium stearate is then screened through a suitable screen, for example, 40 mesh, and the screened magnesium stearate is then added to the blended materials and mixed for 2 minutes. The blended powder is placed in a suitable and properly labeled container and encapsulated in two-piece hard gelatin capsules (size #0) as required.

EXAMPLE 11

Capsule:

Each capsule contains:

| Material | Quantity/350 mg Blend |
|---|---|
| Compound of Formula III | 120.0 mg. |
| Lactose, National Formulary (NF) Fast Flo | 175.0 mg. |
| Microcrystalline cellulose | 18.0 mg. |
| Pregelatinized starch, NF | 35.0 mg. |
| Magnesium stearate, NF | 2.0 mg. |

All of the above-listed materials, except the magnesium stearate, are screened through a suitable screen, for example, 20 mesh, and blended in a mixer for about 5 minutes. The magnesium stearate is then screened through a suitable screen, for example 40 mesh, and the screened magnesium stearate is then added to the blended materials and mixed for 2 minutes. The blended powder is placed in a suitable and properly labeled container and encapsulated in two-piece hard gelatin capsules (size #0) as required.

FORMULAE

-continued
FORMULAE
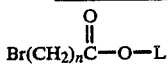 X
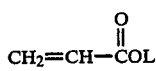 Xa
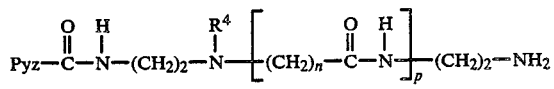 XI
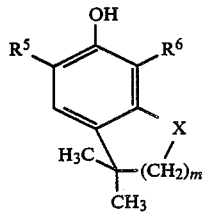 XII
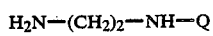 XIII
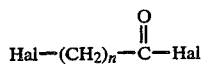 XIV
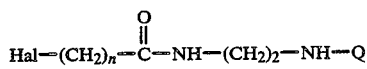 XV
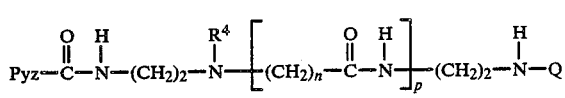 XVI
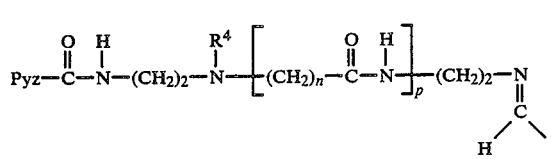 XVII
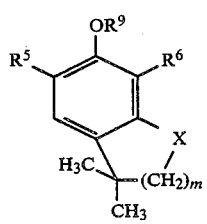 XVIII
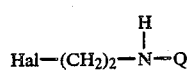 XIX
 XIXa
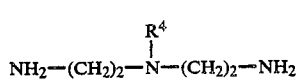 XX
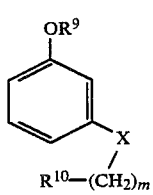 XXI

What is claimed is:

1. A compound having the formula

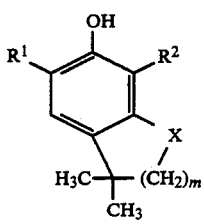

III wherein
one of $R^1$ and $R^2$ is a radical Z wherein Z is chloro bromo iodo trifluoromethyl, methylsulfonyl or aminosulfonyl of formula $-SO_2NR^{10}R^{11}$ in which $R^{10}$ and $R^{11}$ are independently hydrogen or (1–5-C)alkyl;

the other of $R^1$ and $R^2$ is a group having the formula

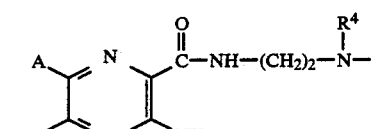

IV

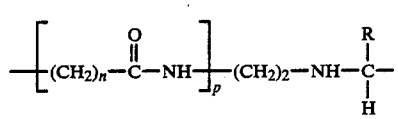

in which
A is chloro or bromo,
$R^4$ is hydrogen or (1–5C)alkyl, n is 1 or 2, p is 0 or 1, and R is hydrogen or methyl;
X is methylene, oxygen or sulfur; and
m is 1, 2, or 3;
or a pharmaceutically acceptable salt thereof.

2. A compound as claimed in claim 1 wherein each of $R^4$, $R^{10}$, and $R^{11}$ is, independently, hydrogen, methyl, ethyl or propyl.

3. A compound as claimed in claim 1, wherein $R^4$ is methyl.

4. A compound as claimed in claim 1, wherein Z is bromo.

5. A compound as claimed in claim 1, wherein A is chloro.

6. A compound as claimed in claim 2, wherein $R^4$ is methyl, Z is bromo and A is chloro.

7. A compound as claimed in claim 1, which is 3,5-diamino-N-[2-[[2-[[(6-bromo-2,3-dihydro-5-hydroxy-1,1dimethyl -1H-inden-4-yl)methyl]amino]ethyl]-methylamino]ethyl]-6-chloropyrazinecarboxamide, or a pharmaceutically acceptable salt thereof.

8. A compound as claimed in claim 1, which is 3,5-diamino-N-[2-[[2-[[(9-bromo-2,3,4,5-tetrahydro-8-hydroxy-5,5-dimethyl-1-benzoxepin-7-yl)methyl-]amino]ethyl]methylamino]ethyl]-6-chloropyraxinecarboxamide, or a pharmaceutically acceptable salt thereof.

9. A pharmaceutical composition comprising a eukalemic diuretic amount of a compound of claim 1 or a pharmaceutically acceptable salt thereof and a pharmaceutically acceptable diluent or carrier.

10. A method of inducing eukalemic diuresis in a mammal comprising administering to said mammal a pharmeceutically effective amount of a compound of claim 1.

11. A method of treating hypertension in mammals comprising administering a pharmaceutically effective amount of a compound of claim 1 to a mammal in need of such treatment.

* * * * *